United States Patent
Braatz et al.

[11] Patent Number: 5,651,357
[45] Date of Patent: Jul. 29, 1997

[54] CONNECTION TO A GAS CYLINDER

[75] Inventors: Robert E. Braatz; Gordon G. Sansom, both of Sun Prairie, Wis.

[73] Assignee: Ohmeda Inc., Liberty Corner, N.J.

[21] Appl. No.: 527,966

[22] Filed: Aug. 14, 1995

Related U.S. Application Data

[63] Continuation-in-part of Ser. No. 244,016, May 13, 1994, abandoned.

[30] Foreign Application Priority Data

Nov. 14, 1991 [GB] United Kingdom ............... 9124195

[51] Int. Cl.$^6$ ................ A62B 9/04; A61M 15/00; A61M 16/10
[52] U.S. Cl. ................... 128/202.27; 128/203.12
[58] Field of Search ............... 128/202.27, 202.22, 128/203.12, 203.26, 204.18, 204.26, 205.22

[56] References Cited

U.S. PATENT DOCUMENTS

| | | |
|---|---|---|
| 1,026,066 | 5/1912 | Wolf. |
| 1,484,108 | 2/1924 | Zoltowski. |
| 2,169,082 | 8/1939 | Stevens et al. ............ 285/108 |
| 2,613,462 | 10/1952 | Johnson ................ 40/10 |
| 3,606,390 | 9/1971 | Taylor ................. 285/39 |
| 3,787,993 | 1/1974 | Lyon ................. 40/306 |
| 3,831,599 | 8/1974 | Needham ............. 128/203.12 |
| 4,015,865 | 4/1977 | Kongelka ............. 285/195 |
| 4,058,120 | 11/1977 | Caparrelli et al. ........ 128/203.12 |
| 4,640,031 | 2/1987 | Hoek et al. ............. 40/306 |
| 4,693,853 | 9/1987 | Falb et al. ............. 128/202.27 |
| 4,825,860 | 5/1989 | Falb et al. ............. 128/203.12 |
| 4,827,643 | 5/1989 | Hearst et al. ............. 40/306 |
| 4,867,212 | 9/1989 | Mohr et al. ............. 128/203.12 |
| 4,883,049 | 11/1989 | McDonald ............. 128/203.12 |
| 5,293,865 | 3/1994 | Altner et al. ............. 128/203.26 |

Primary Examiner—Kimberly L. Asher
Attorney, Agent, or Firm—Roger M. Rathbun; Salvatore P. Pace

[57] ABSTRACT

A system of making a connection between the yoke of an anesthetic delivery apparatus and a gas cylinder for supplying a gas to that apparatus. The system includes an adaptor block that has a keying system, such as pegs, that keys the adapter block into a specific gas cylinder, such as by indentations. The adapter block has machine readable indicia and is affixed to the anaesthesia delivery apparatus such that the apparatus can read the indicia to determine the position of the adaptor block and thus identify the particular gas cylinder that is connected to the adapter block. By this system, a plurality of gas cylinders having differing gases can be used to supply a single inlet of an anesthetic delivery apparatus rather than have a separate inlet for each gas. In each instance, the particular gas thus provided is identified by the anaesthetic delivery apparatus to make the necessary adjustments to that apparatus to administer the gas to a patient.

10 Claims, 4 Drawing Sheets

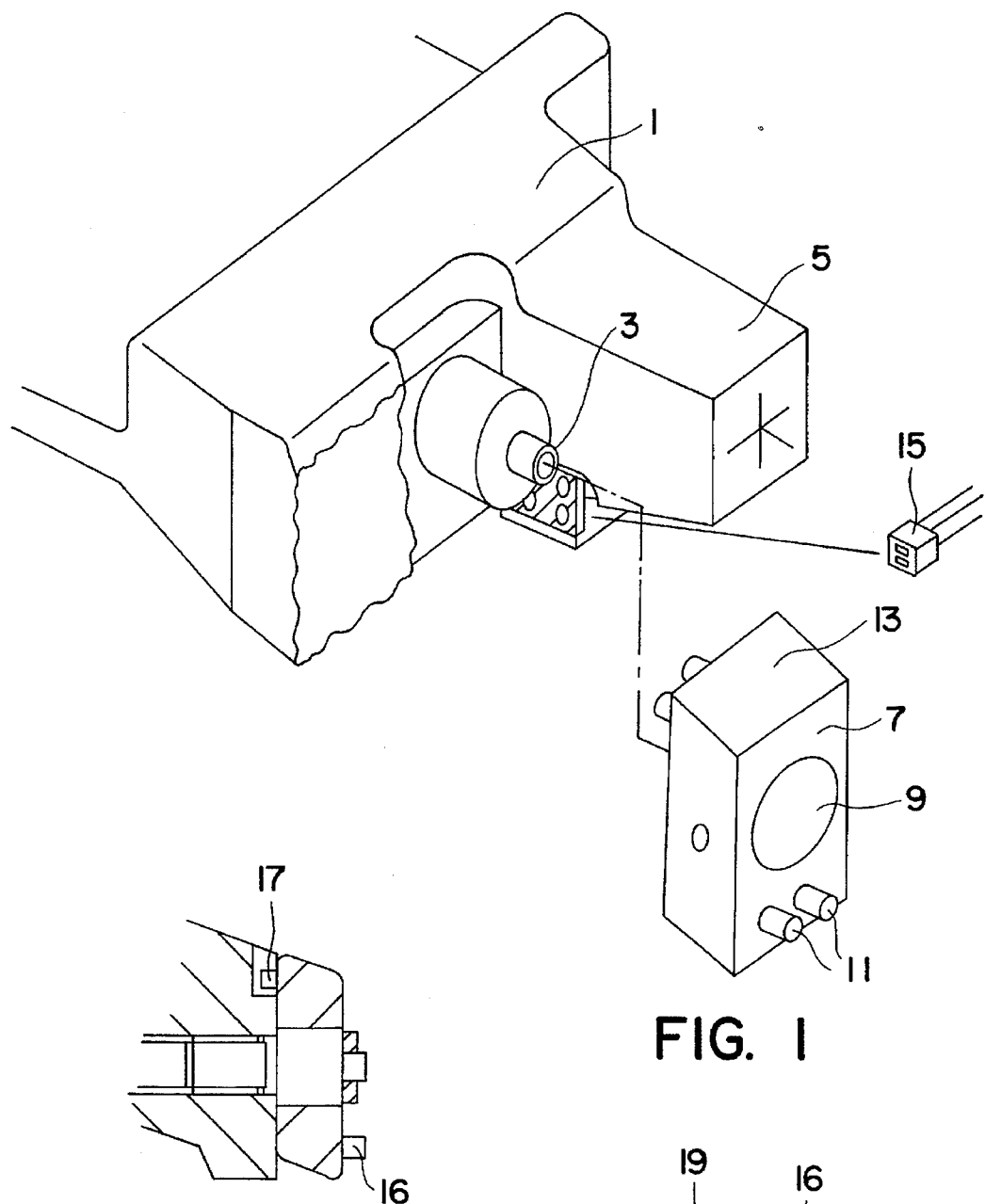
FIG. 1
FIG. 2
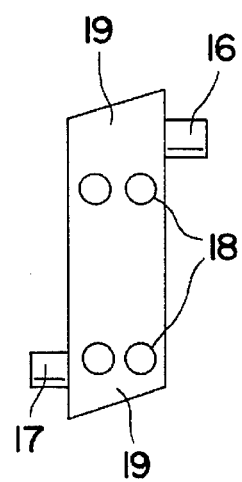
FIG. 3

CONNECTION TO A GAS CYLINDER

This application is a continuation-in-part of U.S. patent application Ser. No. 08/244,016 filed May 13, 1994, now abandoned.

FIELD OF THE INVENTION

The present invention relates to techniques for forming connections to gas cylinders, and to an adaptor or mounting block for use in forming such connections.

BACKGROUND OF THE INVENTION

Anesthesia is commonly induced in a patient by means of an inhaled gaseous mixture comprised of anesthetic agent vapor, oxygen and a balance gas such as nitrous oxide, nitrogen, or helium delivered by an anesthetic gas delivery apparatus. For adequate control of the administration of a drug to a patient, it is essential that, not only the drug, but also the carrier gas be positively and accurately identified to ensure that, amongst other things, the rate of flow of carrier gas can be accurately controlled.

It is known to provide the yoke on the anaesthetic delivery apparatus with formations specific to a particular gas which can mate with corresponding formations on a cylinder containing that gas. The formations and keying systems are covered by recognized industry standards known as ISO 407. The formations on the yoke and the cylinder commonly take the form of cooperating pins and corresponding sockets or recesses respectively. The formations can prevent an incorrect cylinder from being fitted to the yoke.

The use of a series of mating formations on the yoke and the cylinder to identify the gas contained within the cylinder has been found to provide the necessary ability to identify accurately the gas within the cylinder. However, in order for anaesthetic delivery apparatus to be capable of taking a range of gases from respective cylinders, it is necessary for the yokes on which the cylinders are mounted on the apparatus to have formations for mating with each different cylinder type. This can increase the space requirement of the yokes on the apparatus to an unacceptable level. Furthermore, it requires appropriate components to be provided, calibrated for each specific gas, to allow flow of a selected carrier gas from its respective yoke into the delivery apparatus for use.

SUMMARY OF THE INVENTION

In accordance with the present invention, there is provided a technique for connecting a gas cylinder to an anaesthetic delivery apparatus which makes use of machine readable indicia associated with the cylinder containing the gas to ensure that a correct cylinder is connected to the apparatus.

The invention enables a gas cylinder to be mounted on the yoke of anaesthetic delivery apparatus such that the anaesthetic delivery apparatus identifies, and thus recognizes, the particular cylinder and can make the necessary adjustments to its calibration or flow detection for that specific gas.

The apparatus will preferably include means for controlling the flow rate of gas supplied from the gas cylinder. The provision of means for identifying the gas which is being supplied to the apparatus (in the form of the machine readable indicia) allows the flow rate measuring means to be calibrated by the apparatus automatically according to the gas which is being supplied; it is not necessary for the operator of the apparatus to identify the gas which is being supplied and to set up the apparatus accordingly. A further advantage of the apparatus of the invention is that only one path for flow of gas from the cylinder is required. The same path can thus be used for a variety of gases supplied to the apparatus and separate paths for differing gasses is not necessary.

The use of an adaptor block in the connection technique of the invention has the advantage that the yoke provided on the anaesthetic delivery apparatus on which a gas cylinder is to be mounted can be arranged to receive a range of gas cylinders, each gas cylinder having formations on it to identify the gas uniquely. The yoke can be changed to receive a cylinder containing a different gas simply by replacement or repositioning of the adaptor block with respect to the yoke. Appropriate calibration of the apparatus for other gases can take place automatically following identification of the gas by means of the machine readable indicia.

In addition to reducing the space requirement of the gas cylinder mounting components of anaesthetic apparatus, the technique of the present invention has the further advantage of reducing significantly the complexity of the apparatus while allowing the apparatus to receive a number of different gas cylinders containing different gases. Thus it is possible for the apparatus to receive a number of different gas cylinders without the need for a series of valves and associated passageways within the apparatus leading from the multiple cylinder yokes used previously.

The adaptor block may be provided with a single set of formations and machine readable indicia so that it can be used with just a single type of gas cylinder to identify the gas within that cylinder. Preferably, however, the adaptor block is provided with more than one set of formations and indicia so that it can be used with cylinders containing different respective gases. For example, two or more sets of formations may be provided side by side along the adaptor block, each set of formations mating with corresponding formations on cylinders of specific gases. Such an adaptor block can be used on different gases simply by selecting the point at which it is fitted to the yoke. Alternatively, or in addition, formations may be provided on opposite sides of an adaptor block so that the block can be arranged to receive different cylinders simply by reversing the orientation of the block on the yoke. This construction has the advantage that the space requirement of the adaptor block is minimized.

The formations on the adaptor block will be selected to mate with the corresponding formations on the gas cylinder to provide a keying system such that only a specific gas cylinder can be operatively connected to an adaptor having the corresponding keying means in the proper position. A practice of using a system of pins and corresponding recesses for identifying gas cylinders is well established whereby a series of holes on the gas cylinder must align with a series of pegs extending outwardly from the manifold on the anesthesia machine. The system of the present invention may be provided with formations of this type, however, other types of formations or keying means may, of course, be used.

The machine readable indicia, which may be provided on the cylinder or on the adaptor block provided for association with the cylinder, may be readable for example mechanically, optically or magnetically. For example, the indicia might be read mechanically when in the form of appropriate formations such as spring loaded pins which can be received in corresponding recesses, or in the form of recesses for receiving such pins on the cylinder or block.

Such indicia can function also as the formations which allow the cylinder or block to be connected to the apparatus.

Indicia, may be optically encoded; for example, an optically reflective or absorbing material may be provided in a prearranged pattern on the cylinder or adaptor block if present which allows the cylinder to be identified by means of an appropriate light source and detector. For example, in a preferred construction, the cylinder or block may be provided with a pre-determined pattern of material which ensures that light reflected by the cylinder or block has a pattern characteristic of the cylinder (or of that particular face of the block). For example, a series of dots of a non-reflective material may be provided on the cylinder or adaptor block, the pattern of dots being characteristic of the cylinder or block or of the face of the block. This result might be achieved by providing a black material such as a paint on the cylinder or block, preferably within a recess to minimize damage thereto. The indicia reading means might then take the form of a combination of a light source and a detector for the reflected light.

Other forms of indicia on the cylinder or adaptor block include magnetic indicia, for example provided by a magnetically detectable material in a predetermined pattern on the cylinder or block.

Preferably, the indicia provided on the cylinder or adaptor block are arranged so that indicia must be identified by the reading means on the delivery apparatus (indicating to the operator that an cylinder or adaptor block is present on the yoke) in order for the delivery apparatus to operate. For example, in the case of optically detected indicia, it is preferred that they be reflective indicia (so that in the absence of a cylinder or block no optical signal is reflected) rather than transmissive indicia (where the absence of a cylinder or block might not be accurately identified by the reading means in the event of equipment failure). This has the advantage of providing an added level of security in the delivery apparatus, indicating to the operator when no gas cylinder or adaptor block is fitted.

In the preferred embodiment, the system is designed with a 6-bit code for each gas cylinder and there are two reflective areas and two nonreflective areas of indicia. The active signal is applied to all four areas thereby resulting in two active and two blind messages. This sequence gives no sequence of failures that would result in the wrong code being recognized by the system.

Preferably, in addition to the indicia which are read by the reading means on the anaesthetic delivery apparatus, additional indicia are provided on the adaptor block which can be visually read by the operator of the anaesthetic delivery apparatus to indicate the gas cylinder which can be fitted to the adaptor block. For example, the name or an appropriate symbol for the relevant gas might be written on the block. When the block is provided with more than one set of formations and machine readable indicia, more than one set of operator readable indicia will generally also be provided.

In a preferred embodiment, the yoke will comprise a spigot, and the adaptor block will have a passageway extending through it in which the spigot can be received when the adaptor block is mounted on the yoke. The spigot will generally have a passageway extending through it so that gas supplied from the gas cylinder through the passageway in the adaptor block can enter the anaesthetic delivery apparatus through the passageway in the spigot on the yoke. When the adaptor block has more than one set of formations and machine readable indicia for forming connections between the anaesthetic delivery apparatus and gas cylinders containing different gases, the adaptor block may be moved between its positions for connection to the different gas cylinders containing the respective gases by removal from the spigot, and subsequent replacement on the spigot in a different orientation. In another configuration, the adaptor block may be moved between its positions for connection to the different gas cylinders by sliding, for example by rotation in the manner of a dial, or by linear movement.

BRIEF DESCRIPTION OF THE DRAWINGS

Embodiments of the present invention will now be described by way of example with reference to the accompanying drawings, in which, FIG. 1 is an isometric view of components of a gas cylinder mounting apparatus of the present invention;

FIG. 2 is a cross-section through the apparatus shown in FIG. 1;

FIG. 3 is a side elevation of a first embodiment of the adaptor block;

DETAILED DESCRIPTION OF THE PREFERRED EMBODIMENTS

Figure 4:
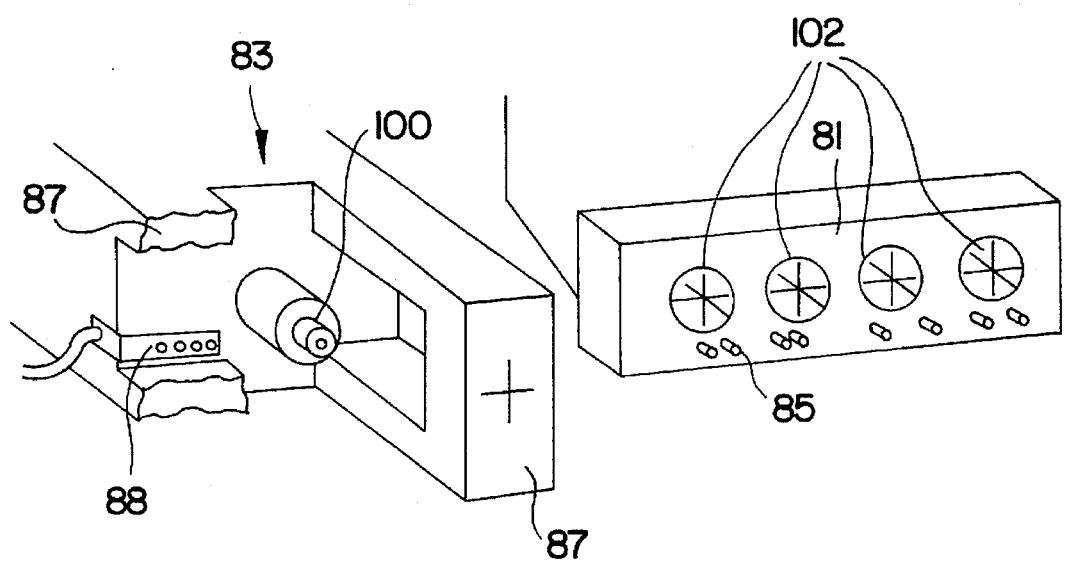
FIG. 4 is an isometric view of a second embodiment of adaptor block; of an anaesthetic delivery apparatus which includes a third embodiment of adaptor block.

Referring to the drawings, FIG. 1 shows a gas cylinder mounting apparatus which includes a yoke 1 having a hollow spigot 3 extending from it. Carrier gas passes from a gas cylinder into the yoke 1 through the opening in the spigot 3. The spigot 3 extends between two guide arms 5, only one of which is shown in FIG. 1.

An adaptor block 7 has an opening 9 extending through it in which the spigot 3 is received. The adaptor block 7 is provided with a number of features which are specific to a gas in the cylinder to be connected to the adaptor block 7. These features include a pair of identification pins 11 which can be received in corresponding recesses on the cylinder. The adaptor block 7 further includes machine readable indicia (which cannot be seen in the FIG. 1 view), and optionally, the chemical formula of the gas which can be supplied through the adaptor block 7.

The gas cylinder mounting apparatus further includes means for reading the indicia on the adaptor block 7, which comprises a series of reflective opto-switches 15, that is, each opto-switch has its own light source and receiver. Obviously, however, individual light sources and detectors may be used. The opto switches 15 are mounted on the guide arm 5 adjacent to the spigot 3. The opto switches both transmit and detect the light reflected from the indicia on the adaptor block 7. The light signals may be coded by frequency or timing characteristics.

The adaptor block 7 shown in FIG. 1 to 3 has two series of features which allow the adapter block 7 to form connections between the yoke 1 and a cylinder containing either of two gases, by appropriate selection of the orientation of the adaptor block 7 on the yoke 1. Each set of features comprises pins, machine readable indicia, and a label for the operator of the apparatus to identify the gas in question.

Turning to FIG. 2, there is shown the apparatus of FIG. 1 with the adaptor block 7 assembled to the yoke 1. As can be seen, a first set 16 of pins is provided on the face of the adaptor block 7 on which a gas cylinder is received and a second set 17 of pins is likewise provided on the face of the adaptor block 7 remote from the side receiving the gas cylinder.

FIG. 3 is a side view of the adaptor block shown in FIG. 1 showing the side hidden from view in FIG. 1. The adaptor block 7 has two sets 16, 17 of pins. The block is provided with two sets of machine readable indicia 18, each set of indicia corresponding to one of the sets of pins 16, 17 indicative of the gases in question. The selection of the features on the adaptor block 7 for forming a connection between the yoke 1 and a gas cylinder can be made by rotation of the adaptor block 7 about an axis extending perpendicular to the plane of the page of drawings.

As can be seen, therefore in the FIG. 1–3 embodiment, the adaptor block 7 can be positioned on to the yoke 1 with either set 16 or 17 facing outwardly to receive a similarly keyed gas cylinder. Since each set 16, 17 has different pin spacing in according with conventional practice. the positioning of the adaptor block 7 on the yoke 1 will determine what gas cylinder may be affixed to the adapter 7 and hence, what gas will be introduced into the yoke 1 to be delivered by the anaesthetic delivery apparatus.

Since, different indicia are provided on the adaptor block 7 associated with each set of pins 16, 17, the optical detector 15 is able to read the corresponding indicia on the adaptor block 7 and determine its position and, as explained, will therefore also know what gas is being delivered form a gas cylinder.

Therefore, the same yoke 1 may be used for the connection to two differing gas cylinders by changing the position of the adaptor block 7 and the anaesthetic delivery machine does not require two yokes to receive two differing gas cylinders, yet, in each position of the adaptor block 7, the machine can read the machine readable indicia on the adaptor block 7 and therefore will readily identify the particular gas and make the necessary adjustments to the flow controller etc of the anaesthetic delivery apparatus.

FIG. 4 shows an adaptor block 81 which can be used to form connections between a yoke 83 and four different gas cylinders, by appropriate selection of the position of the adaptor block 81 on the yoke 83. To this end, the adaptor block 81 is provided with four sets of features including pins 85. Also included are labels and machine readable indicia (not shown in the FIG. ). The block 81 is moved relative to the yoke 83 by pulling it outwardly and then sliding the adapter block 81 along a path defined by bridge sections 87.

As can be seen, the adaptor block 81 can be set in any one of the four positions and slid into position on the yoke 83 such that the hollow spigot 100 will pass through one of the four openings 102 in the adaptor block 81. In this case, the machine reading indicia is, of course, located on the back side of the adaptor block 81 and therefore not shown in the FIG.

A device 88 is provided on the yoke for reading indicia on the block 81 associated with each set of connection pins 85. Accordingly, when the appropriate opening 102 is selected depending on the particular gas cylinder, the appropriate set of pins 85 will allow only that particular gas cylinder to be affixed to the hollow spigot 100 for supplying gas to the anaesthetic delivery apparatus. The device 88 will then read the proper machine readable indicia that corresponds to that gas and therefore, the apparatus obtains the correct information as to the gas being delivered.

In the FIG. 4 embodiment, therefore, the adaptor block 82 is simply moved in a linear path to locate the appropriate opening, engaging the adaptor block 82 at that location with the hollow spigot 100 to thereby receive the correct gas from the gas cylinder.

Figure 5:
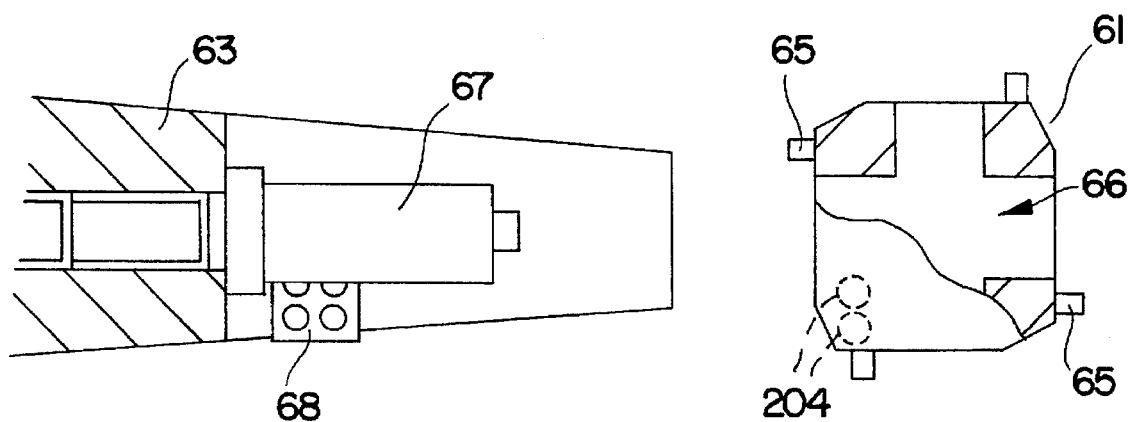
FIG. 5 is an isometric view of yet another embodiment of the subject invention.

FIG. 5 shows an adaptor block 61 which also can be used to form connections between a yoke 63 and four different gas cylinders by appropriate selection of the orientation of the adaptor block 61 on the yoke 63. To this end, the adaptor block 61 is provided with four sets of features including pins 65 and associated crossing bores 66 in which the spigot 67 on the yoke 63 can be received. Also included are labels and machine readable indicia 204 as depicted on the far side of the adaptor block 61. The orientation of the block 61 on the spigot 67 is altered by removal from the yoke 63 and appropriate rotation. A device 68 is provided on the yoke 63 for reading the indicia on the adaptor block 61 associated with each set of connection pins 65.

Accordingly, again, the adaptor block 61 may be used to connect any one of four gas cylinders to a yoke 67 to introduce four differing gases to the anaesthetic delivery apparatus by a simple rotation of the adaptor block 61. In each of the four positions, a set of pins 65 will allowing the conventional keying to a specific gas cylinder and, for each of the four positions, appropriate machine reading indicia align with the reading device 68 so that the anaesthetic delivery apparatus can determine the position of the adaptor block 61 and thus, the identity of the gas that is being received by the spigot 67.

As indicated earlier, in the Figures, the preferred indicia is some indicia that is machine readable by an optical reader, that is, by a conventional light source and light detector that simply directs the light signal onto the indicia and the return light is sensed by the detector. Other means of indicia and means for reading the same could include mechanical or magnetic means.

Figure 6:
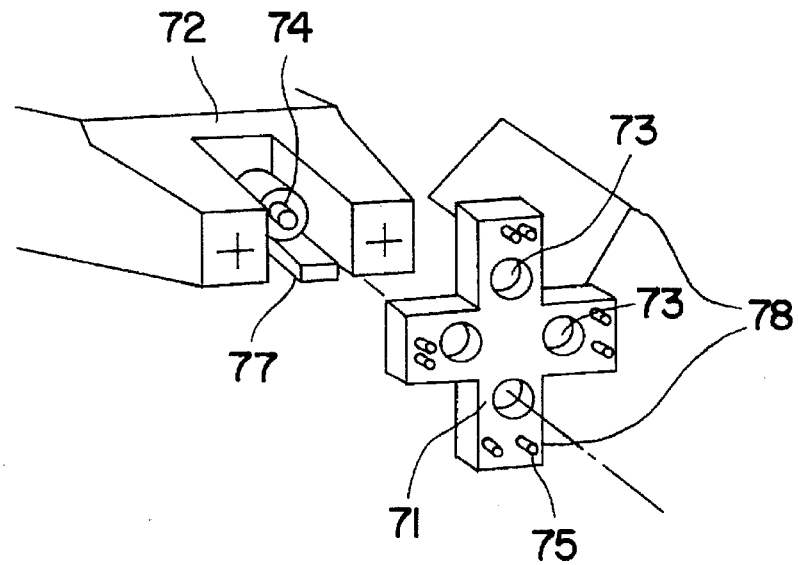
FIG. 6 is an end elevation of a fourth embodiment of adaptor block.

FIG. 6 shows still another construction of an adaptor block 71 which can be used to form connections between a yoke 72 and four different gas cylinders by appropriate selection of the orientation of the adaptor block 71 on the yoke 72. The adaptor block 71 in this embodiment has four openings 73 through which a spigot 74 on the yoke 72 can extend and four sets of pins 75 which can be received in appropriate recesses on respective gas cylinders. The orientation of the adaptor block 71 is altered by removal from the yoke 72 and rotation of the adaptor block 71 to a different position, in this case at 90 degree positions. A device 77 is provided on the yoke 72 for reading indicia 78 on the block 71 associated with each set of connection pins 75.

Again, therefore, the adaptor block 71 may be moved between any one of four positions and each position, the appropriate indicia on the adaptor block 71 for a particular gas cylinder is read by a reading device located on the yoke 72 so that the anesthetic delivery apparatus can learn which gas is being delivered to the system.

Figure 7A:
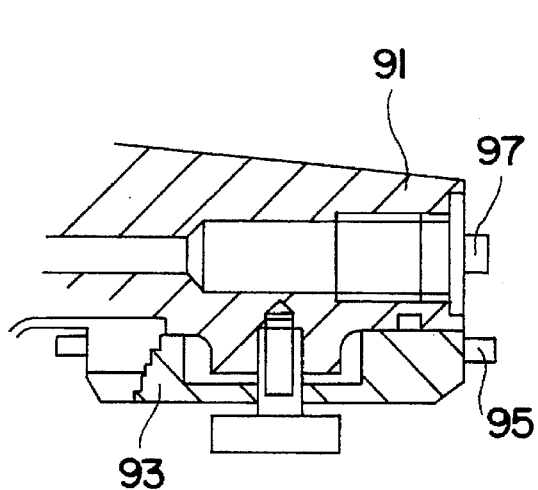
FIGS. 7(a) and (b) are side (partially in section) and end views, respectively, of a yoke for a gas cylinder with an associated adaptor block.
Figure 7B:
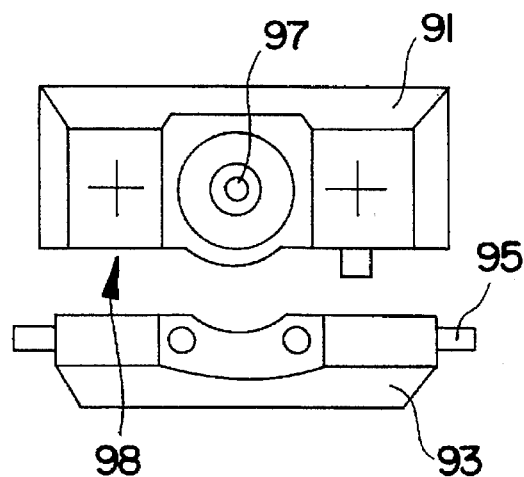

FIGS. 7(*a*) and 7(*b*) show a yoke 91 which has an adaptor block 93 mounted on a side face. The adaptor block 93 again has pins 95 extending from its face outwardly to key with an appropriate keying system on a gas cylinder and is further mounted to the yoke 91 so that the adaptor block 93 has the pins 95 adjacent to spigot 97 on which a gas cylinder can be mounted. The pins 95 on the adaptor block 93 are arranged for mating with respective cylinders of gases when mounted on the spigot 97, and the yoke 91 can be adapted for use with a selected gas by means of the orientation of the adaptor block 93 on the yoke 72.

The adaptor block 93 bears machine readable indicia (not shown) and appropriate labels, and the yoke 91 bears a device 98 for reading the indicia on the block.

Figure 8A:
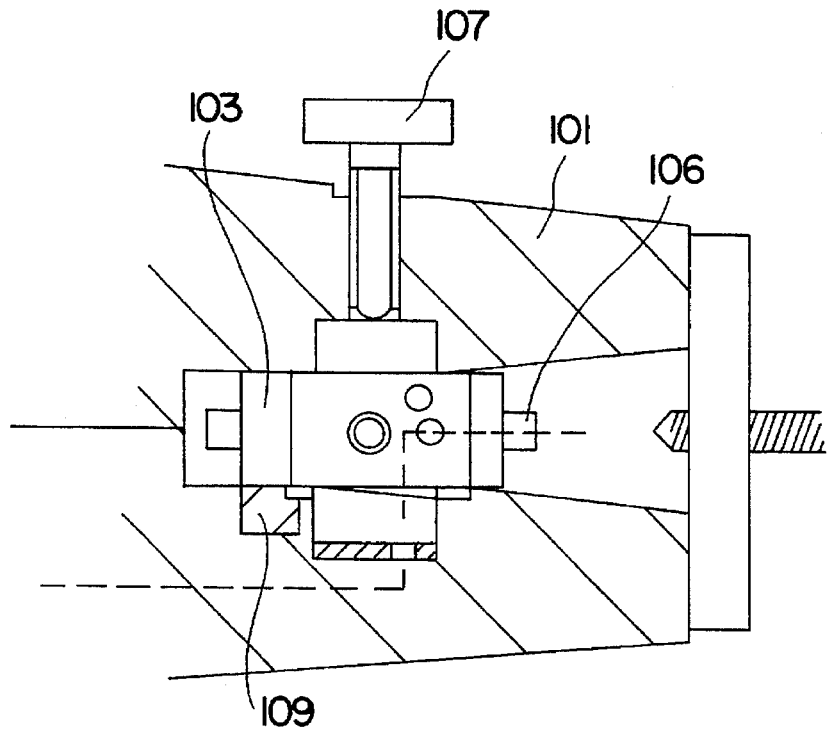
FIGS. 8(a), (b) and (c) are side (partially in section), plan (partially in section), and end views, respectively, of a yoke to which an adaptor block is fitted.
Figure 8B:
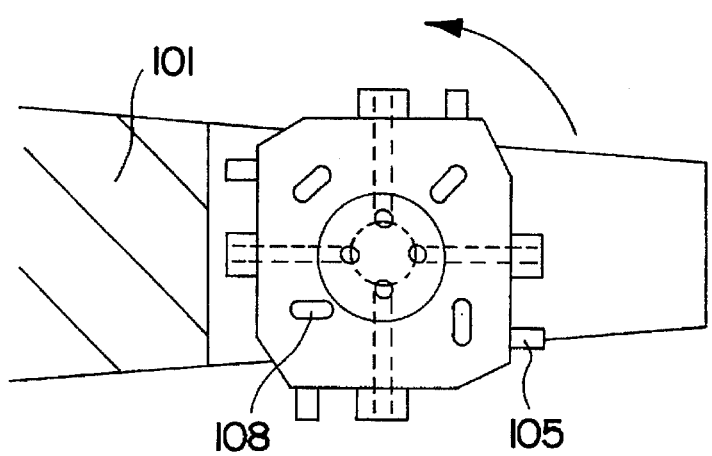
Figure 8C:
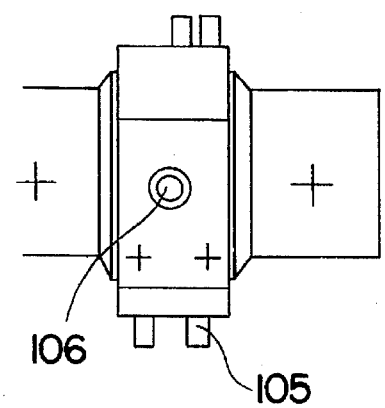

FIGS. 8(a), 8(b) and 8(c) show a yoke 101 which has an adaptor block 103 permanently and rotatably mounted on it. Gas received from a cylinder passes into the adaptor block 103 and into the anaesthesia delivery apparatus for mixture with an anaesthetic agent through the hub on which the block rotates, as shown by the dotted line 104. The adaptor block 103 has pins 105 extending from each of its faces, and a bore 106 associated with each set of pins 105 for connection to the gas outlet on a gas cylinder. The pins 105 on faces of the adaptor block 103 are arranged for mating with respective cylinders of gases, and the yoke 101 can be adapted for use with a selected gas by orienting the adaptor block 103 through rotation thereof with respect to the yoke Orientation of the adaptor block 103 is carried out by untightening the clamp 107 to allow the adaptor block 103 to be rotated, rotating the adaptor block 103 so that the desired face with its pin(s) 105 is aligned with the cylinder to be connected to the yoke 101, and then retightening the clamp 107. The adaptor block bears machine readable indicia 108 and appropriate labels, and the yoke 101 bears a device 109 for reading the indicia on the block.

We claim:

1. An anaesthetic delivery apparatus adapted to be connected to a gas cylinder for receiving gas from the gas cylinder for delivery to a patient, said anaesthetic delivery apparatus comprising:
   (a) a gas cylinder mounting yoke having an opening for receiving gas from a gas cylinder connected thereto,
   (b) an adaptor block affixed to said yoke, said adapter block having a plurality of keying means to interfit with differing specific gas cylinders to allow the gas from a specific gas cylinder to enter said opening in said yoke,
   (c) a plurality of machine readable indicia on said adaptor block, at least one of said indicia being indicative of the specific gas contained within the specific gas cylinder interfitted to said keying means,
   (d) means for reading said machine readable indicia on said adaptor block to identify said gas in said gas cylinder being delivered to said gas cylinder mounting yoke.

2. An anaesthetic delivery apparatus as defined in claim 1 wherein said machine readable indicia on said adaptor block is optically readable.

3. An anaesthetic delivery apparatus as defined in claim 2 wherein said machine readable indicia comprise optically reflective and absorbing materials in a prearranged pattern.

4. An anaesthetic delivery apparatus as defined in claim 1 wherein said adaptor block includes visual indicia readably by an operator to identify the gas cylinder affixed to the adaptor block.

5. An anaesthetic delivery apparatus as defined in claim 1 wherein said adaptor block has opposed surfaces and said keying means is located on each of said opposed surfaces of said adaptor block, said adaptor block being affixable to said yoke in either of two positions with one of said opposed surfaces positioned to receive a gas cylinder with the appropriate gas cylinder having a compatible keying means.

6. An anaesthetic delivery apparatus as defined in claim 1 wherein said adaptor block is affixable to said yoke in each of a plurality of positions for affixing one of a plurality of differing specific gas cylinders, said adaptor block being mounted to said anaesthesia delivery apparatus for sliding movement with respect to said yoke to select each of said plurality of positions.

7. An anaesthetic delivery apparatus as defined in claim 1 wherein said adaptor block is affixable to said yoke in each of a plurality of positions for affixing one of a plurality of differing specific gas cylinders, said adaptor block being mounted to said anaesthesia delivery apparatus for rotary movement with respect to said yoke to select each of said plurality of positions.

8. An anaesthetic delivery apparatus adapted to be connected to a specific gas cylinder for receiving gas from the gas cylinder for delivery to a patient, said anaesthetic delivery apparatus comprising:
   (a) a gas cylinder mounting yoke, said yoke having a gas spigot extending outwardly therefrom having a predetermined outer diameter, said spigot having a passageway for receiving gas from a gas cylinder connected thereto,
   (b) an adaptor block having a plurality of openings, each of a predetermined inner diameter and adapted to fit around said yoke to be affixed thereto, said adapter block having keying means to interfit with a specific gas cylinder to allow the gas from the specific gas cylinder to enter said passageway in said yoke,
   (c) a plurality of machine readable indicia on said adaptor block, at least one of said indicia being indicative of the specific gas contained within the gas cylinder interfitted keying means,
   (d) means for reading said machine readable indicia on said adaptor block to identify said gas in said gas cylinder being delivered to said gas cylinder mounting yoke.

9. An anaesthetic delivery apparatus as defined in claim 8 wherein said plurality of openings are arranged aligned in a row in said adaptor block.

10. An anaesthetic delivery apparatus as defined in claim 8 wherein said plurality of openings comprises four openings spaced in a cross pattern in said adaptor block.

* * * * *